US008989472B2

(12) United States Patent
Porikli et al.

(10) Patent No.: US 8,989,472 B2
(45) Date of Patent: Mar. 24, 2015

(54) METHOD FOR SIMULATING THORACIC 4DCT

(71) Applicant: Mitsubishi Electric Research Laboratories, Inc., Cambridge, MA (US)

(72) Inventors: Fatih Porikli, Watertown, MA (US); Feng Li, Quincy, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 165 days.

(21) Appl. No.: 13/765,757

(22) Filed: Feb. 13, 2013

(65) Prior Publication Data

US 2014/0226884 A1 Aug. 14, 2014

(51) Int. Cl.
  G06K 9/00 (2006.01)
  G06F 19/00 (2011.01)
  A61N 5/10 (2006.01)
  G06T 17/20 (2006.01)

(52) U.S. Cl.
  CPC .......... *G06F 19/3437* (2013.01); *A61N 5/1037* (2013.01); *G06T 17/20* (2013.01); *G06T 2200/08* (2013.01); *G06T 2210/41* (2013.01)
  USPC .............................................. 382/131; 703/2

(58) Field of Classification Search
  None
  See application file for complete search history.

(56) References Cited

U.S. PATENT DOCUMENTS

| 6,396,496 | B1 * | 5/2002 | Pfister et al. ................. 345/427 |
| 7,421,122 | B2 * | 9/2008 | Kaus et al. ................... 382/173 |
| 7,925,068 | B2 * | 4/2011 | Hoctor et al. ................. 382/132 |
| 7,966,134 | B2 * | 6/2011 | German ........................ 702/41 |
| 8,265,363 | B2 * | 9/2012 | Orderud et al. ............... 382/128 |
| 2008/0194957 | A1 * | 8/2008 | Hoctor et al. ................. 600/443 |
| 2009/0129650 | A1 * | 5/2009 | Hawkes et al. ............... 382/131 |
| 2009/0284529 | A1 * | 11/2009 | De Aguiar et al. ........... 345/420 |
| 2011/0093243 | A1 * | 4/2011 | Tawhai et al. ................. 703/2 |

OTHER PUBLICATIONS

A. Didier, P. Villard, J. Saadé, J. Moreau, M. Beuve, and B. Shariat. A chest wall model based on rib kinematics. In Visualisation, 2009. Second International Conference in, pp. 159-164. IEEE, 2009.
J. Eom, C. Shi, X. Xu, and S. De. Modeling respiratory motion for cancer radiation therapy based on patient-specific 4DCT data. In MICCAI 2009, pp. 348-355, 2009.
A. Hostettler, S. Nicolau, C. Forest, L. Soler, and Y. Remond. Real time simulation of organ motions induced by breathing: First evaluation on patient data. Biomedical Simulation, pp. 9-18, 2006.
J. Saadé, A. Didier, P. Villard, R. Buttin, J. Moreau, M. Beuve, and B. Shariat. A preliminary study for a biomechanical model of the respiratory system. In the International Conference on Computer Vision Theory and Applications, 2010.

(Continued)

*Primary Examiner* — Hadi Akhavannik
(74) *Attorney, Agent, or Firm* — Dirk Brinkman; Gene Vinokur

(57) ABSTRACT

Four-dimensional (4D) computed tomography (CT) is simulated by first generating a surface mesh from a single thoracic CT scan. Tetrahedralization is applied to the surface mesh to obtain a first volume mesh. Finite element analysis, using boundary constraints and load definitions, is applied to the first volume mesh to obtain a lung deformation according to an Ogden model. Constrained tetrahedralization, using control points, is applied to the lung deformation to obtain a second volume mesh, which is then deformed using mass-spring-damper simulation to produces the 4DCT.

18 Claims, 8 Drawing Sheets

(56) References Cited

OTHER PUBLICATIONS

Behr et al. "Modelling, Visualization, and Interaction techniques for Diagnosis and Treatment Planning in Cardiology," Computers and Graphics, vol. 24, No. 5. Oct. 1, 2000.
Sermesant et al. "Deformable Biomechanical Models: Application to 4D Cardiac Image Analysis," Medical Image Analysis, vol. 7, No. 4. Dec. 1, 2003.

Wei-Te et al. "A 5D Model for Accurate Representation and Visualization of Dynamic Cardiac Structures," Proceedings of SPIE, vol. 3911, May 3, 2000.
Bueno et al. "Three-Dimensional Organ Modeling Based on Eformable Surfaces Applied to Radio-oncology," Journal of Zhejiang University: Science C, vol. 11, No. 6, Jun. 2010. pp. 407-417.

* cited by examiner

METHOD FOR SIMULATING THORACIC 4DCT

FIELD OF THE INVENTION

The invention relates generally to four-dimensional, computed tomography (4DCT), and more particularly to simulating respiration for radiotherapy treatment planning.

BACKGROUND OF THE INVENTION

The use of four-dimensional computed tomography (4DCT) is a common practice in radiation therapy treatment planning for thoracic regions. The information from 4DCT allows a radiation oncologist to plan accurate treatments for moving tumors, deliver radiation within predetermined certain interval in the breathing cycle, and reduce the risk of treatment-related side effects.

Methods for 4DCT include retrospective slice sorting, and prospective sinogram selection. For the retrospective slice sorting method, the projection data are continuously acquired for a time interval longer than a respiratory cycle. Multiple slices corresponding to different times are reconstructed and sorted into respiratory phase bins using various respiratory signals. For the prospective sinogram selection method, the scanner is triggered by the respiratory signal. Then, the projection data within, the same phase bin are used to reconstruct CT slices corresponding to that breathing phase.

Both methods are time consuming and considerably increase the radiation dose for the patient. For example, the radiation dose of a conventional 4DCT scan is about six times a typical helical CT scan, and 500 times a chest X-ray. Moreover, 4DCT acquisition alone cannot determine the tumor position in-situ. These facts are a major concern in the clinical application of 4DCT, motivating development of advanced 4DCT simulators.

Various methods are known for modeling lung inflation and deflation. The first category of methods discretize the soft tissues and bones into masses (nodes), and connect the nodes using springs and dampers (edges) based on a mass-spring-damper system, and CT scan values for spline-based mathematical cardiac-torso (MCAT) phantoms, augmented reality based medical visualization, respiration animation, and tumor motion modeling. A common approach applies affine transformations to control points to simulate respiratory motion. Lungs and body outline are linked to the surrounding ribs for synchronized expansion and contraction. Those simple and fast methods only provide approximate lung deformations when compared with accurate models based on continuum mechanics.

The second category of methods use hyperelastic models to describe the non-linear stress-strain behavior of the lung. To simulate lung deformation between two breathing phases $(T_i, T_{i+1})$, the lung shape at phase $T_{i+1}$ is used as the contact or constraint surface, and deform the lung at phase $T_i$ based on the predefined mechanical properties of lung. A negative pressure load is applied on the lung surface, and finite element (FE) analysis is used to deform tissues. The lung expands according to the negative pressure, and slide against the contact surface to imitate the pleural fluid mechanism. The pressure can be estimated from the pleural pressure versus lung volume curve, which measured from a pulmonary compliance test.

In addition to lung deformation, the displacements of the rib cage and diaphragm are also very important to design a realistic 4DCT simulator. Rib cage motion can be a rigid transformation. A finite helical axis method can be used to simulate the kinematic behavior of the rib cage. The method can be developed into a chest wall model relating the ribs motion to thorax-outer surface motion for lung simulation.

A simple diaphragm model includes central tendon and peripheral muscular fiber. Then, cranio-caudal (CC) forces are applied to each node of the muscular fiber to simulate the contraction of the diaphragm. A Gauchy-Green deformation tensor can model the lung deformation. Organs inside the rib cage can be considered as a convex balloon to estimate an internal deformation field directly by interpolation of skin marker motions.

SUMMARY OF THE INVENTION

The embodiments of the invention provide a method for simulating thoracic 4DCT. The method uses a biomechanical motion model that can faithfully simulate deformation of the lung and nearby organs for an entire respiration cycle. Deformations of other organs can also be simulated.

As an advantage, the method only requires a single CT scan as input. Loads on the rib cage and the diaphragm constrain the deformation of the lung. This distinguishes the present method from conventional continuum mechanics based methods. The method can also simulate a passive mass-spring model based deformation of abdominal organs due to respiration.

The lung stress-strain behavior is modeled using a hyperelastic model. The lung deformation problem is solved by finite element (FE) analysis. Diaphragm control points and spine regions are segmented out to carefully define the boundary conditions and the load definitions, and to improve FE convergence using a mesh optimization procedure.

The remaining CT volume is treated as discretized mass points connected by springs and dampers. The motion of liver, bones and other organs can be simulated using finite difference analysis.

This heterogeneous design can leverage the advantages of both continuum mechanics and mass-spring-damper system in the way that the lung deformation is modeled with a very high accuracy, while the deformation of the rest of the CT volume is achieved under practical computation constraints.

DETAILED DESCRIPTION OF THE PREFERRED EMBODIMENTS

Thoracic 4DCT Simulator Method

Figure 1:
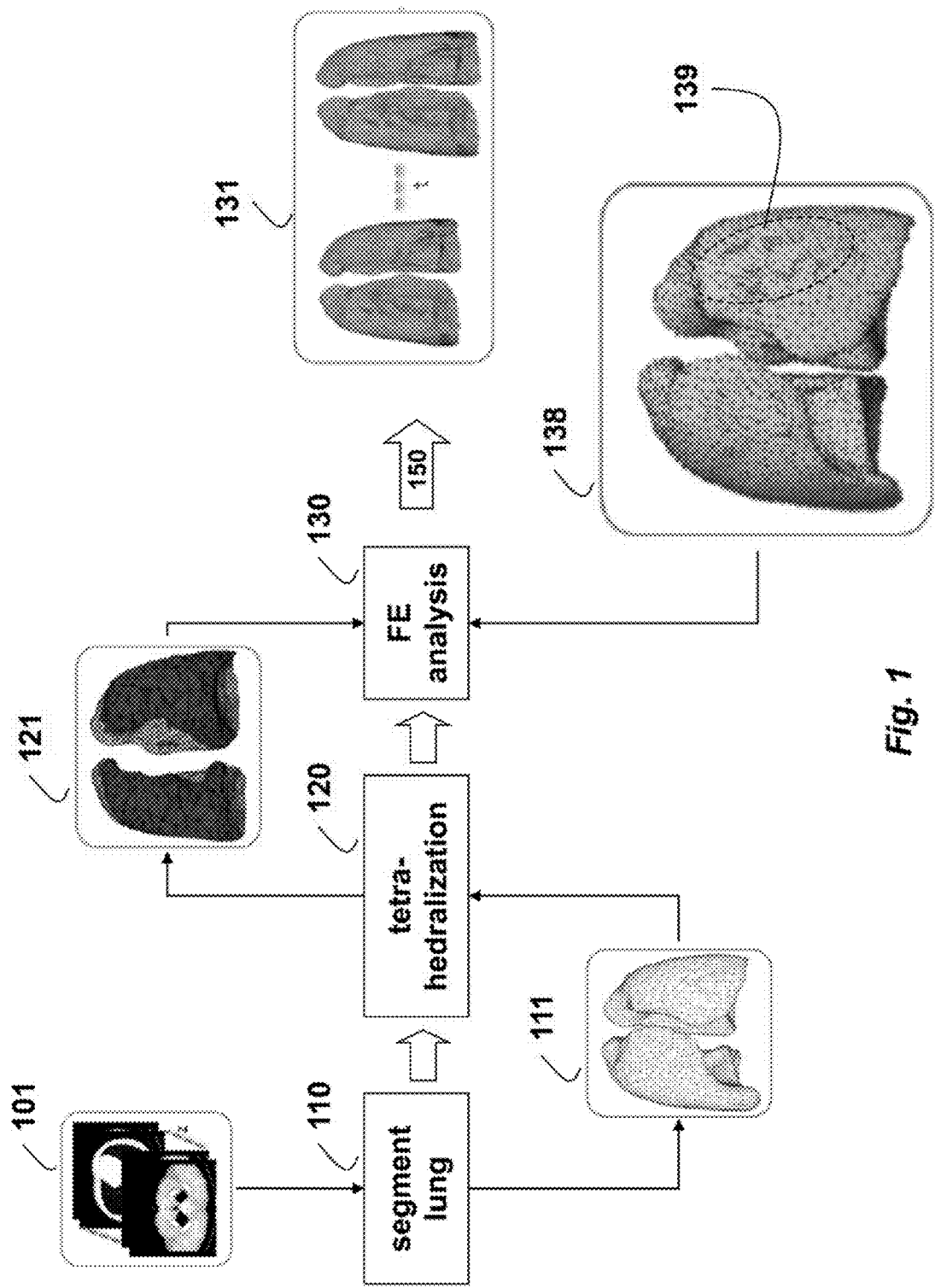
FIGS. 1 and 2 are flow diagrams of a method for simulating thoracic 4DCT according to embodiments of the invention.
Figure 2:
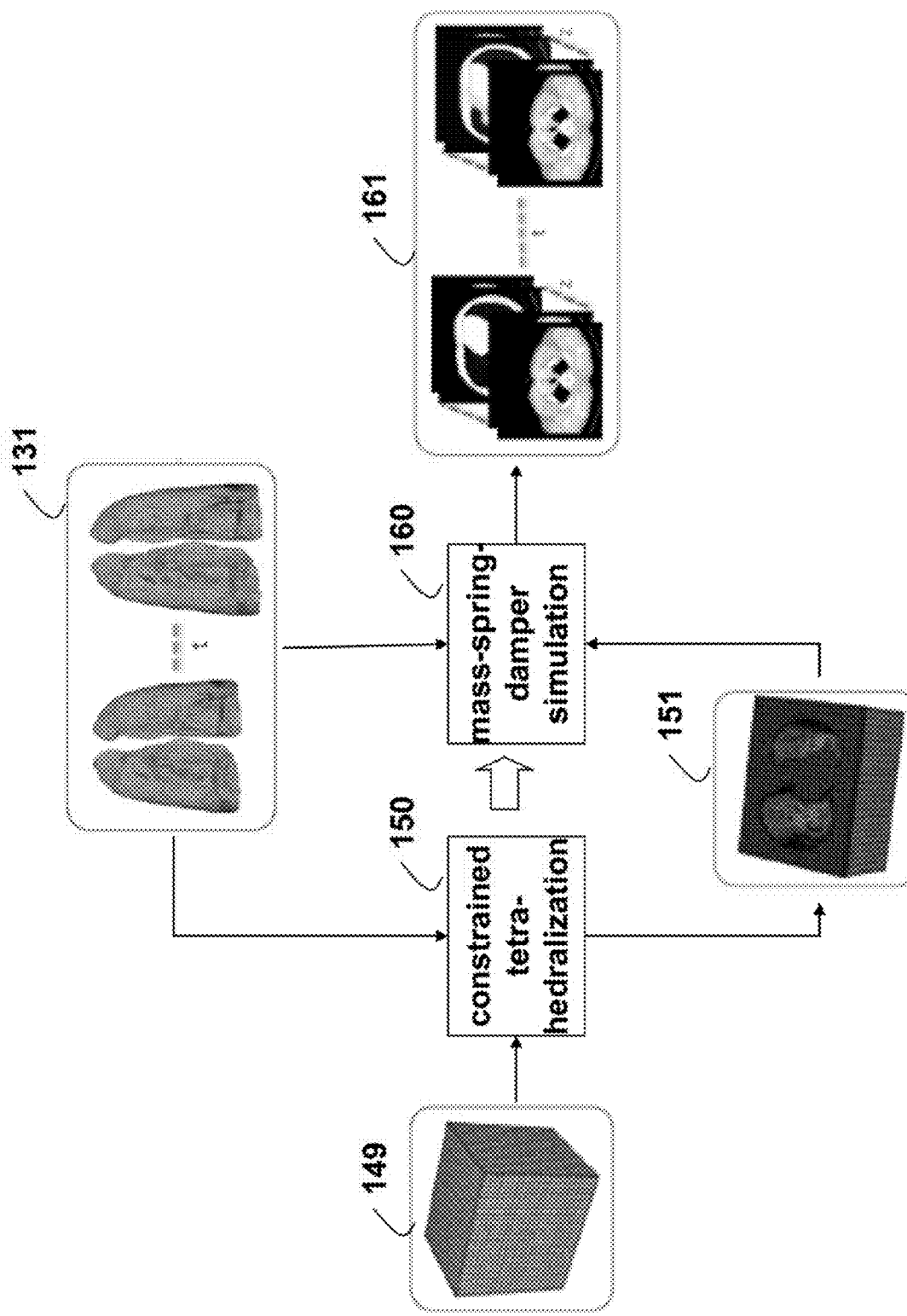

FIGS. 1 and 2 show a processing pipeline of a thoracic four-dimensional computed tomography (4DCT) simulator method according to embodiments of the invention. The method includes lung deformation and 4DCT scan simulation. The method can be performed in a processor connected to memory and input/output interfaces as known in the art. It should be understood that the invention can also be used to simulate other types of tissue or organ deformations, and utilize other types of medical scans known in the art.

Input to the method is a single thoracic CT scan 101. The CT scan is segmented 110 to generate a surface mesh 111 of the lung. Tetrahedralization 120 is applied to the surface mesh to obtain a first volume mesh 121.

Finite element (FE) analysis 130, using boundary constraints and load definitions 138, are applied to the first volume mesh to obtain a lung deformation 131. The lung deformation is according to an Ogden model, wherein the lung is modeled using a hyperelastic function based on nonlinear continuum mechanics, such that the tumor motion trajectories inside the lung are accurate.

Continuing with in FIG. 2, constrained tetrahedralization 150, using control points 149, is applied to the lung deformation 131 to obtain a second volume mesh 151, which is a refinement of the first volume mesh. The refined mesh coincides with or is partly or entirely outside the first volume mesh. In other words the second mesh corresponds to a refined organ volume. That is, the refined organ volume accurately represent the actual shape of the organ during the simulation.

Then, mass-spring-damper simulation 160 produces the simulated thoracic 4DCT 161. The mass-spring-damper model is used to deform the CT volume. Thus, segmentation of rig cage, spines, and other organs, as in the prior art, is unnecessary.

Our simulator can generate any desired number of lung deformations between a maximal exhale phase $T_{ex}$ and the maximal inhale phase $T_{in}$, which are used to synthesize the corresponding 4DCT phases.

The method can construct 4DCT phases with or without hysteresis of the tissue deformation, which defines how the lung; volume is correlated with the inhale-to-exhale motion path and the exhale-to-inhale motion path. Without hysteresis, the CT scan for the same lung volume states are identical regardless of whether the lung is in the inhale-to-exhale cycle or the inhale-to-exhale cycle.

For a particular lung volume, our method assembles the corresponding 4DCT phases to generate a simulated sequence of CT's. In addition to the lung volume, pleural pressure and chest and abdomen height can also be used to synchronize for real-time patient-specific 4DCT, as described below.

The method steps described herein can be performed in a processor connected to memory and input/output interfaces as known in the art.

Biomechanical Motion Model for Simulation of Lung Deformation

Boundary Constraints

For simplicity of notation, we use x, y, and z to represent lateral, anteroposterior (AP), and superoinferior (SI) direction, respectively. For the lung deformation, we define three types of boundary constraints on the lung surface based on the anatomy and function of the human respiratory system. Because the upper lobes of the lung are constrained by the ribs, the z displacement of the corresponding region are fixed in our simulator to avoid pure translation of the lung in the z direction when simulating the diaphragm contracting on the bottom lobes. Intuitively, the top 5% of the surface vertices in the z direction are selected to represent the upper lobes.

During inspiration, the lung sliding against the rib cage mainly occurs in the posterior spine region, while in the anterior region, the lung expands with the increasing of thoracic cavity and the relative sliding is negligible. Thus, we define the boundary conditions for both the front and the back parts of the lung surface to simulate the different sliding actions. Our method fixes the z displacement for all the points, generally 139 in FIG. 1, to simulate the coherent motion of the lung with the thorax expansion on the axial plane. The selection of these vertices is implemented by the heuristics that the points are on or near a convex hull of the lung surface, around the lateral sides of the middle and lower lobes, and have small normal variations, e.g., <20°.

To simulate the pleural sliding in the spine region, our simulator method automatically locates the lung surface vertices near the thoracic vertebrae, and fixes the x and y displacements of these points as the third boundary constraint. Our goal is to find surface vertices close to the spine. Therefore, we use a Gaussian curve fitting process to locate these points instead of adopting a complicated thoracic vertebrae segmentation approach, as in the prior art.

The idea is to fit a set of Gaussian curves, such that the area cut out by each curve is maximized. This provides a global approximation to the spine shape, and the constraint points can be accurately located.

Figure 3:
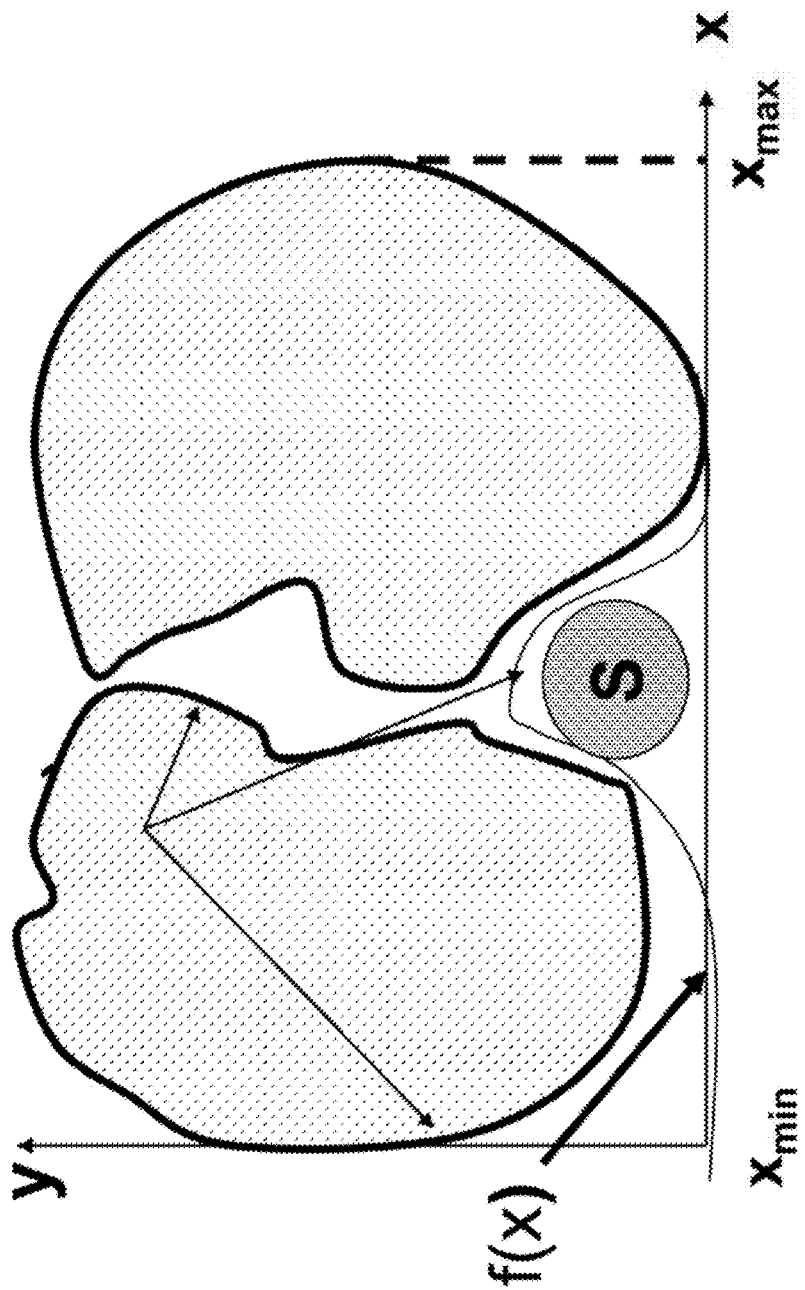
FIG. 3 is a sample 2D axial view for a maximized region covered a Gaussian function according to embodiments of the invention.

FIG. 3 shows a sample 2D axial view, in which our procedure maximizes the spine region S covered, by the Gaussian function $$f(x) = ae^{-\frac{(x-b)^2}{2c^2}}.$$

We formulate the Gaussian function as a constrained multivariable minimization problem $$\min_{a,b,c} - \sum_{x=x_{min}}^{x_{max}} f(x), \text{ s.t. } f(x) - g(x) \leq 0, \forall x \in [x_{min}, x_{max}], \quad (1)$$

where the parameters a, b, and c represent a scaling factor, an expected value, and a standard variance of f(x), $x_{min}$ and $x_{max}$ are limits on the lung in the lateral direction, and g(x) is an upper limit for f(x), and is the minimal y value of the lung slice at each x.

In our simulator, this constrained minimization problem is solved efficiently by a sequential quadratic programming method, specifically an active-set procedure, which determines a sequential quasi-Newton approximation to the Hessian matrix of the Lagrangian multiplier at each iteration. We extend this 2D procedure to the 3D CT volume by applying the procedure slice by slice.

Outliers can occur in the top and bottom of the lung where g(x) is only partial constrained for the curve fitting. Our simulator removes the outliers different than a mean Gaussian curve of the set so that correct fittings of the thoracic vertebrae are retained. The missing curves can be estimated by linear interpolation of the remaining curves.

Loads Definitions

Because there is no hounding surface during inhalation, we design an extra traction applied on the diaphragm area of the lung besides the negative intra-pleural surface pressure. The pressure force inflates the lung in all directions during inspiration, while the traction allows additional displacement in the z direction to simulate the diaphragm contraction and pleural sliding. Hence, the lung surface mesh is likewise inflated during the simulation.

The pressure force is defined from the simulator input. Therefore, we focus on accurately locating the points that are close to the diaphragm for the definition of the traction. We model this as a graph search problem, solve the problem by a modified shortest closed-path procedure.

Figure 4:
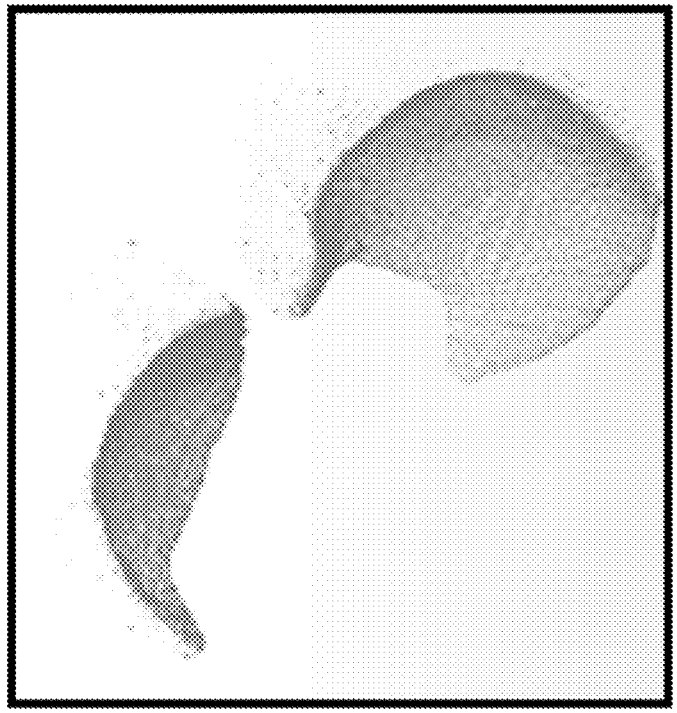
FIG. 4 is an image of a dense 3D point cloud for lung voxels according to embodiments of the invention.

As shown in FIG. 4, our simulator first determines a dense 3D point cloud by finding the lung voxels at every (x,y) location with the largest z value.

Figure 5:
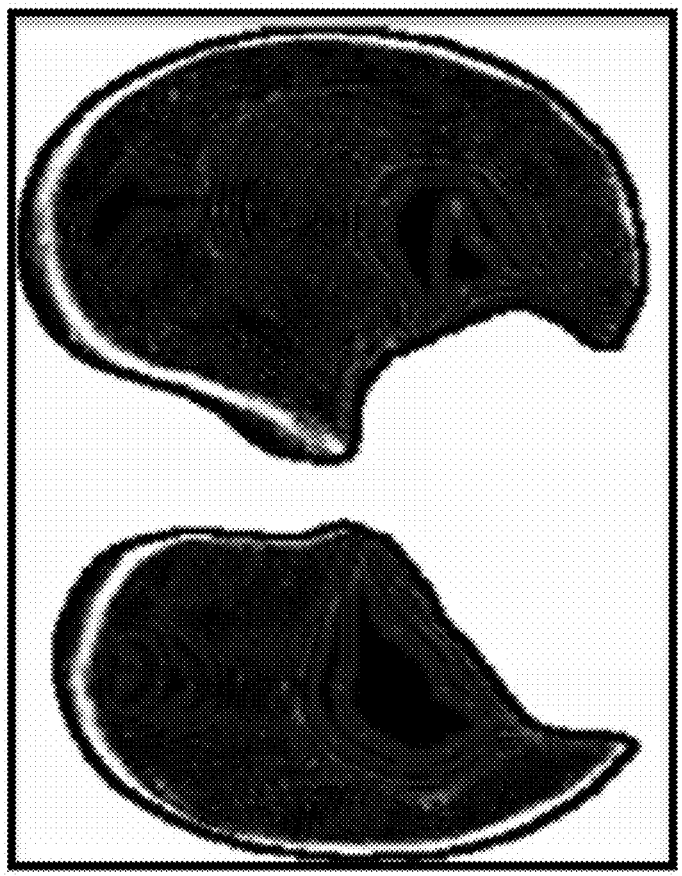
FIG. 5 is an image of the lung after converting the point of FIG. 4 cloud into a weight map according to embodiments of the invention.

As shown in FIG. 5, we convert the point cloud into a weight map based on the local geometry information, and locate the diaphragm points using our modified shortest closed-path procedure. The left and right, lower lobes are treated separately.

Weight Map

We consider the 3D point cloud as an 2D image with intensity value from the z value of the corresponding point, and run a local line direction discrepancy (LDD) computation on this image to generate a weight map W. Thus, our weight map computation is a special type of image filtering.

Figure 6:
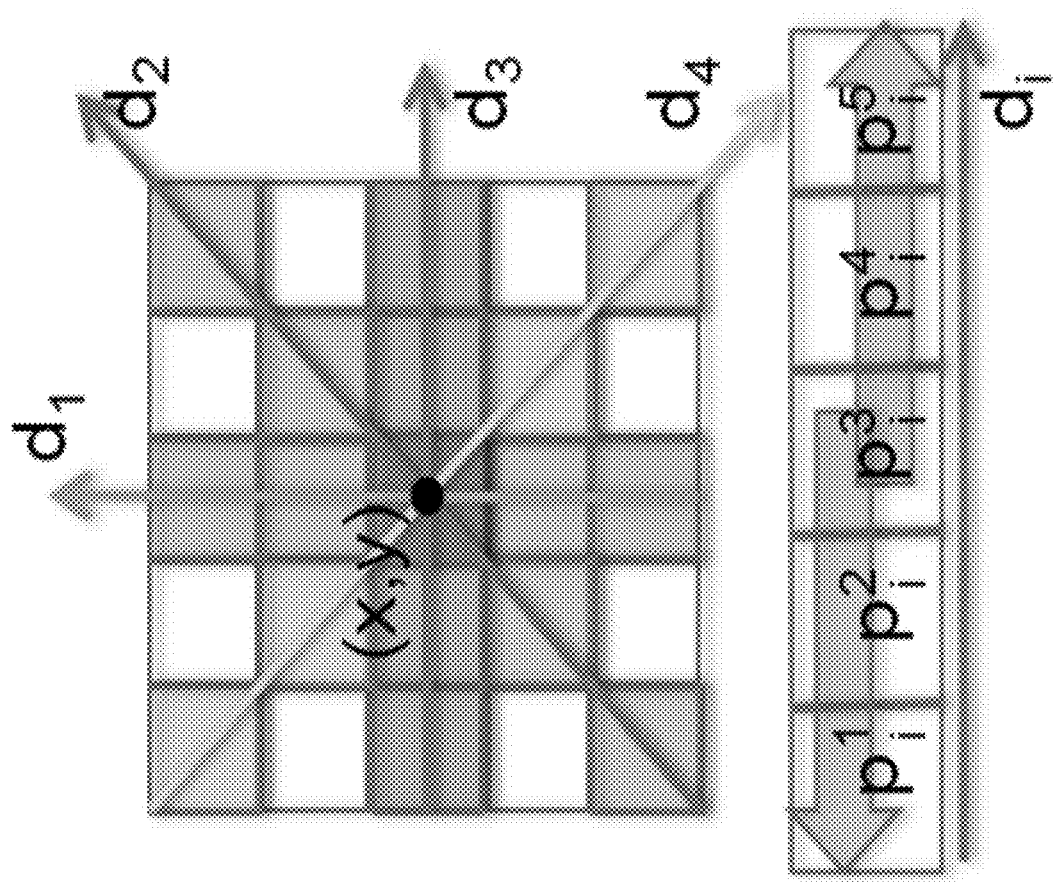
FIG. 6 is a sample weight map according to embodiments of the invention.

As shown in FIG. 6 for each line $d_i(x,y)$ of a block centering at (x,y), we construct two sub-lines $d_i^1(x,y)$ and $d_i^2(x,y)$ from $(p_i^3, p_i^2, p_i^1)$ and $(p_i^3, p_i^4, p_i^5)$ respectively, (i=1, ..., 4), and determine the LDD as the minimum intersection angle of the four sub-line pairs.

Figure 7:
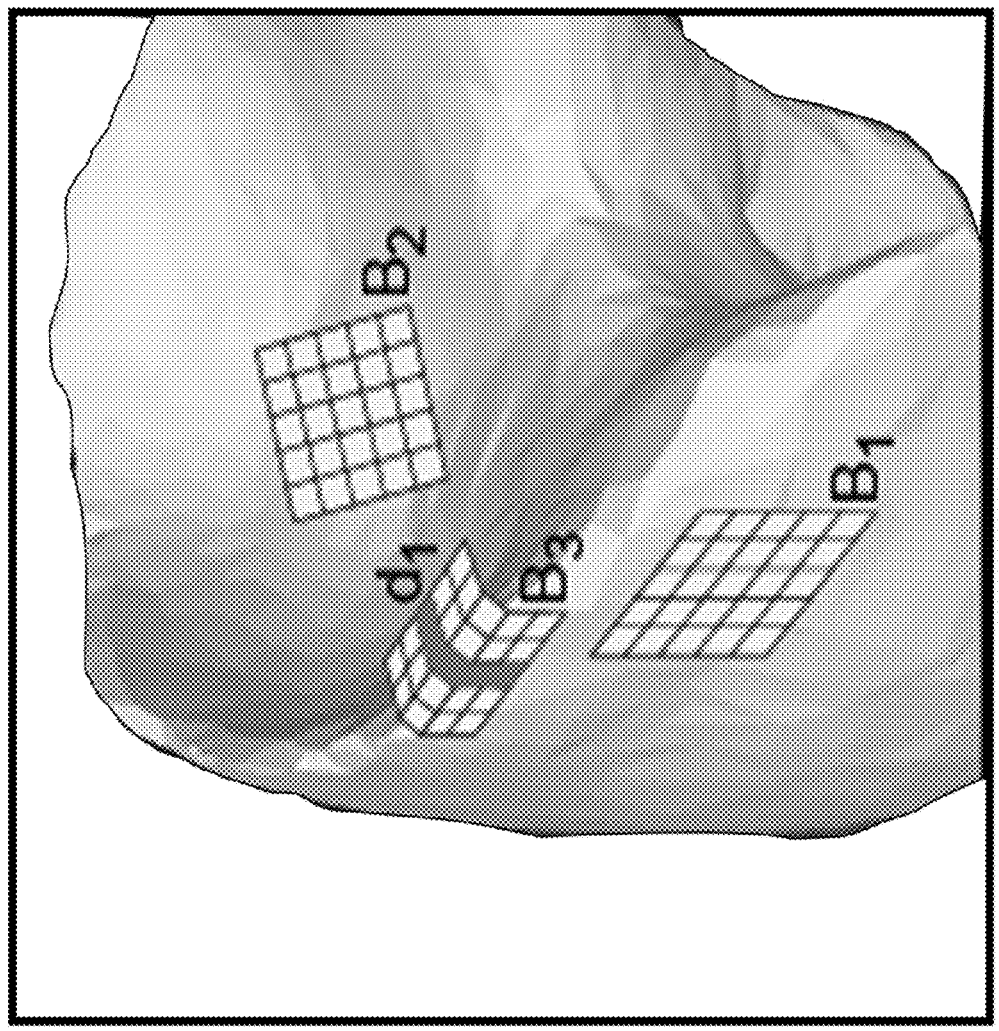
FIG. 7 is a schematic of sample blocks on the lung surface for a weight calculation procedure accord in to embodiments of the invention.

Alternatively, we can determine the maximum of the cosine value of these angles to represent the weight, which can be determined by a dot product as $$W(p) = \max_{i=1,\ldots,4} \left\{ \frac{d_i^1 \cdot d_i^2}{\|d_i^1\| \cdot \|d_i^2\|} \right\}, \quad (2)$$

where p represents pixel position (x,y), and the block size is 5×5, for simplicity. Intuitively, regions with high curvature have high positive LDD values, for example, $d_1$ of $B_3$ in FIG. 7, while flat regions have low negative LDD values, for example, $B_1$ and $B_2$.

Diaphragm Point Segmentation

Notice that all outliers are located at the boundary of the weight map. Therefore, we formulate the diaphragm point segmentation as a shortest closed-path (SCP) problem, which finds a optimal cut along the boundary that separates the diaphragm points from the outliers. To construct the graph for SCP, we select four neighborhood connection and set the edge weight $E_{pq}$ as W(q). Therefore, $E_{pq}$ and $E_{qp}$ can have different weights, instead of using the entire weight map to construct the graph.

Figures 8, 9:
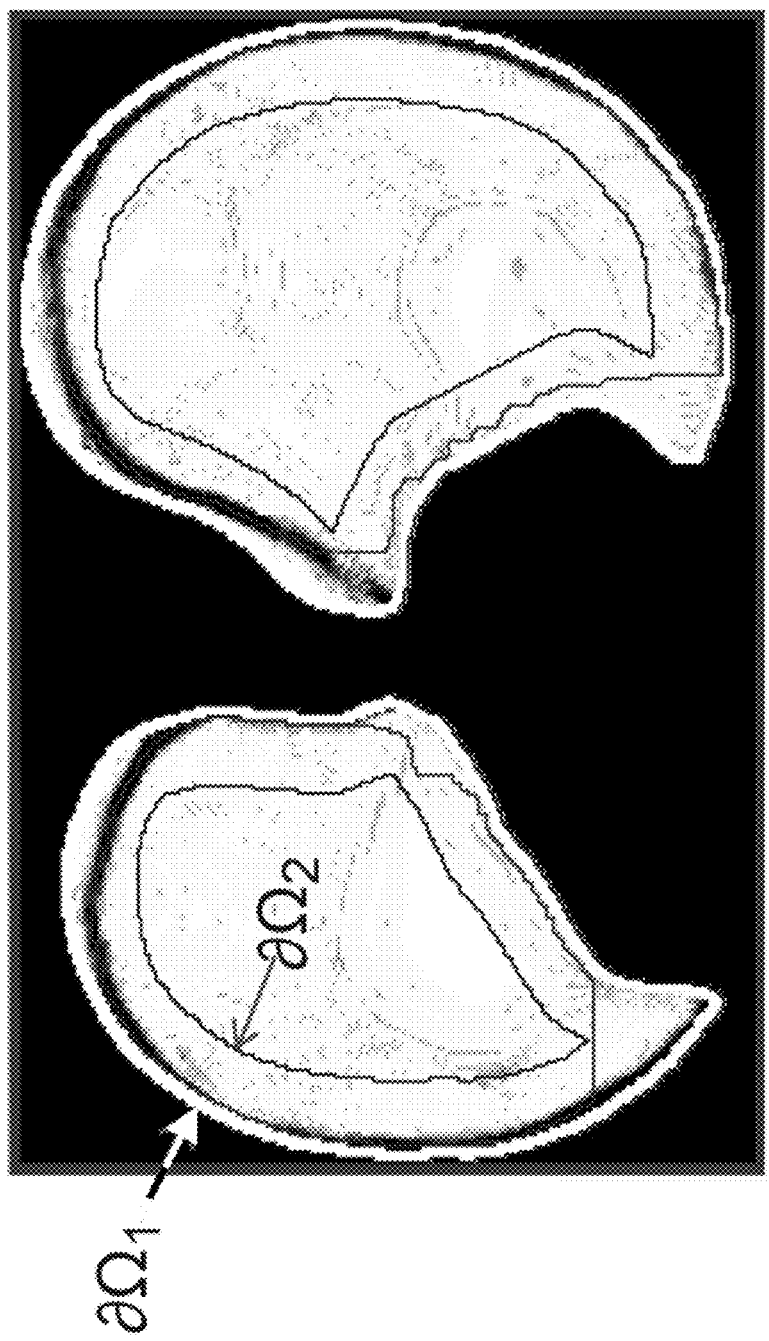
FIG. 8 is a schematic of masking an inner region of the lung from an outer boundary according to embodiments of the invention.
FIG. 9 is a schematic of a ribbon formed after the masking of according to embodiments of the invention.

As shown in FIG. 8, we mask out the inner region with morphological operations, and limit an optimal cut between the inner boundary $\partial\Omega_2$ and the outer boundary $\partial\Omega_1$. If we use the conventional SCP procedure, then some interior regions can be cut out to favor the lowest cost. Instead, we first sample the outer boundary $\partial\Omega_1$ every ten points, and locate the corresponding points, in terms of Euclidean distance, on the inter boundary $\partial\Omega_2$.

For the remaining points on the outer boundary $\partial\Omega_1$, we determine their matches on the inner boundary $\partial\Omega_2$ by linear interpolation of the previous matches, such that there are no crossing matches (lines) and correct ordering is maintained. In this way as shown in FIG. 9, we can "unbend" the ring region between $\partial\Omega_1$ and $\partial\Omega_2$ into a flat ribbon by alignment in order, and set the length of the ribbon as the length of the outer boundary $\partial\Omega_1$, and the width as the shortest distance between outer boundary $\partial\Omega_1$ and the inner boundary $\partial\Omega_2$. Then, we construct a new adjacency matrix graph from the ribbon for the SCP procedure. This yields an accurate model for the diaphragm for the traction definition.

Finite Element Simulation

The final step for biomechanical simulation of lung deformation according to embodiments of the invention is to define the material property of the lung and apply the FE analysis. We assume the lung tissue is homogeneous, isotropic, and use a first-order Ogden model. The well-known Ogden model is a hyperelastic material model used to describe the non-linear stress-strain behavior of complex materials such as biological tissue. The Ogden model, like other hyperelastic material models, assumes that the material behavior can be described by means of a strain energy density function, from which the stress-strain relationships can be derived. These materials can generally be considered to be isotropic, incompressible and strain rate independent. Other models that can be used include a Mooney-Rivlin model, a linear elastic model, a linear viscoelastic model, or combinations thereof.

The Ogden odd describes a non-linear strain energy density function as $$W(\lambda_1, \lambda_2, \lambda_3, J) = \frac{\mu_1}{\alpha_1}(\lambda_1^{\alpha_1} + \lambda_2^{\alpha_1} + \lambda_3^{\alpha_1} - 3) + \frac{K}{2}(\ln J)^2, \quad (3)$$

where $\lambda_{1,2,3}$ are the deviatoric principal stretches, $\mu_1$ and $\alpha_1$ are material constants, J is the Jacobian matrix for the lung deformation, and K is a bulk modulus selected sufficiently high to satisfy near-incompressibility. For the parameters of the Ogden model, we use e.g., $\mu_1$=0.0329, and $\alpha_1$=6.82.

We combine all the information (meshes, loads, and boundaries) defined above into a single script file and directly run the FE analysis to simulate the lung deformation using FEBio developed at the University of Utah Musculoskeletal Research Laboratories. FEBio is an open source nonlinear finite element solver specifically designed for biomechanical applications. One important reason that we choose FEBio is that it is specifically designed for biomechanical applications, and offers constitutive models and boundary conditions that are relevant to the modeling of soft tissue deformation. The wide range of boundary interactions supported in FEBio makes the modeling of pleural sliding very straightforward.

4DCT Scan Simulation

The deformation of the rest of the CT volume is very complicated if we were to use a prior art continuum mechanics based method, which requires segmenting out all the soft tissues, organs, bones, and other structures, and manually defining different material properties and their corresponding boundary constraints. Instead, we treat the rest of the CT volume as a discrete structure of elements and model the CT volume deformation using a mass-spring simulation system.

System Element Definitions

We construct the mass-spring system by sampling control points (masses) in the CT volume excluding the lung region. Then, we connect these points using a constrained Delaunay tetrahedralization procedure to form the links (springs), as a cutting plane. To define mass values for each control points, we first determine their physical densities from the CT image values, i.e., Hounsfield units (HU). The conversion from density to mass is straightforward. The HU versus electron/physical densities curve for human organs and tissues is available for specific CT devices, e.g., $$\rho(x) = \begin{cases} 1.1e^{-3} \cdot h(x) + 1.060 & \text{if } h(x) < -13, \\ 6.0e^{-4} \cdot h(x) + 1.081 & \text{otherwise,} \end{cases} \quad (4)$$

where ρ(x) represents the physical density g/cm³ at position x, and h(x) HU value.

The guideline to define spring constants for the mass-spring system is to assign large values to relatively dense bones, small values to soft tissues, lung, blood, air, etc. based on their HU values. Considering the HU value for bones ranging from +700 to 3000 (dense bone), we nonlinearly map the HU values [700, 3000] to spring constants [0.8 1] based on the reciprocal of an exponential function, while the spring constants of other materials are mapped to [0.001 0.8]. Other heuristic mappings are also possible and have little impact on the system performance.

Dynamics and Forces

We deform the rest of the CT volume based on the lung deformation at each breathing phase. Therefore, our system is an unforced version of a conventional mass-spring-damper system, that is, the external force $F_{ext}=0$. The input is the prescribed displacements of the lung surface vertices, which generates the tensions for the internal springs by Hooke's Law after each lung deformation. We also add damping force $F_d$ to reduce the amplitude of system oscillations. Thus, from Newton's second law, the total force of the system $F_{tot}$ is equal to the internal force $F_{int}$, and defined as $$F_{tot} = F_{int} = F_s + F_d = m \cdot \frac{d^2 y}{dt^2}, \quad (5)$$

where $F_s$ is the spring tension defined as $F_s=-k\cdot y$, $F_d=-\cdot dy/dt$, k is the n×1 spring constant vector, y is the displacement vector of the n control points, m is the mass vector corresponding to the control points, and operator denotes the inner product of two vectors. We define the system as a critically damped system, therefore, the damping factor $R=2\sqrt{m\cdot k}$. Thus, Eqn. 5 can be derived as, $$m\cdot\ddot{y}+R\cdot\dot{y}+k\cdot y=0, \quad (6)$$

where the dots above the variables indicate the respective, derivatives.

We solve this dynamic system using a finite difference method. Between each iteration, we fix the motion of mass points covered, by the spine region to simulate the stationary spine movement. After we have the deformation of the control points, we can determine the deformations of all voxels by trilinear interpolation. Other interpolation method, such as, tricubic interpolation, can also be used to obtain smoother and continuous differentiable volumes.

Volume Mesh Generation

To generate the lung volume mesh for the FE analysis of the lung deformation, we use 3D tetrahedralization of the surface mesh. We can highlight image regions where user labeling could improve the segmentation results. However, because the tetrahedralization is for general purpose segmentation and not specialized for lung segmentations, additional mesh editing may be required to fix small missing pieces and holes. The number of surface vertices can be reduced to ~4000 using quadric edge collapse decimation for simplification. After the surface mesh is given, the lung simulation can run automatically.

Figure 10:
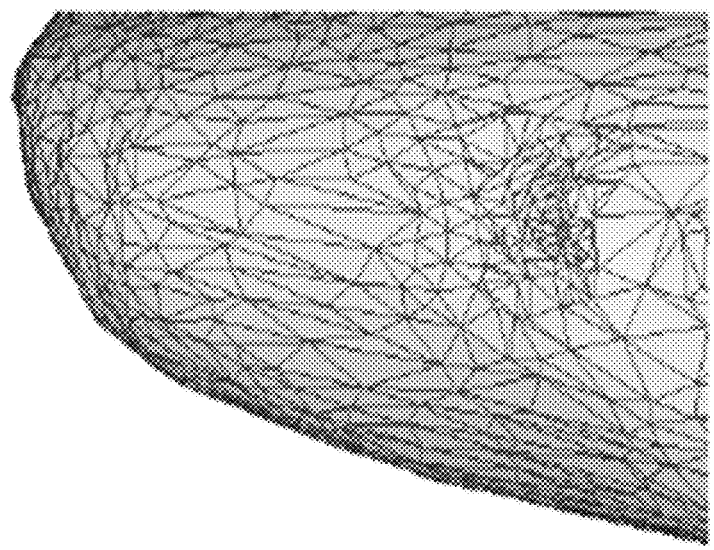
FIG. 10 is a schematic of an irregular surface mesh according to embodiments of the invention.

FIG. 10 shows a portion of a surface mesh. One common problem of the surface mesh generated from segmentation tools is that the mesh is highly irregular, and contains many thin triangles and over-sampled regions. This can lead to badly shaped elements during the 3D Delaunay tetrahedralization process and delay convergence of biomechanical simulations. To optimize the surface mesh, our simulator converts the surface mesh into a solid volume, and then determines a remeshed surface using a marching cube procedure over the volume. This mesh optimization can also fix many other problems with the segmentation results, for instance, self-intersecting faces and non-manifold edges and vertices.

Figure 11:
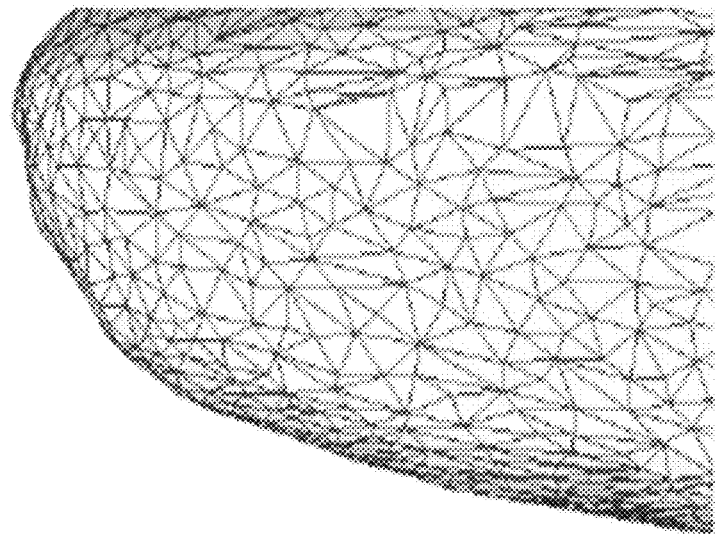
FIG. 11 is a schematic of an optimized surface mesh according to embodiments of the invention.

FIG. 11 shows that the optimized surface contains well-shaped triangles and uniformly sampled vertices, which constitute a valid basis for 3D Delaunay tetrahedralization.

Our biomechanical motion simulation method for lung deformation is very accurate considering a very low spatial resolution of the CT data (0.97×0.97×2.5 mm), especially in z direction. The method works well in the lower posterior region of the lung where nodal displacement is mostly prominent. This indicates that our lung deformation simulator can provide valuable location-specific tumor motion in to significantly reduce the margins between clinical target volume (CTV) and planning target volume (PTV) to potentially improve survival rates for lung-cancer patients.

4DCT Scan Simulation

To generate simulated 4DCT scans, we treat the lung deformation as the equivalent force that drives the deformation of the CT volume because we have already considered all the influencing factors, for instance, the movement of body outline and diaphragm, into the biomechanical simulation of lung deformation. Therefore, or every lung deformation, we can determine its corresponding CT volume deformation through our nonlinear mass-spring-damper system.

During, our simulation, the abdominal organs are squeezed down during rib cage expansion, while the spines are fixed at the same time. This demonstrates that our simulator is capable of providing realistic deformation and displacement of liver, bones, and other soft tissues besides the accurate respiratory motion of lung.

Tumor Embedding

In our simulator, tumors can be embedded into the lung volume mesh through determining barycentric coordinates of their vertices to nearby lung tetrahedra. During X-ray images integration, we can also synthesize the ground truth 3D tumor contours. By putting different types of tumor at different positions of the lung, our simulator is able to provide unbiased ground truth for validating the accuracy of different, tumor tracking algorithms. Compared with X-ray videos with metallic markers, our X-ray images remove the side effects of high Contrast regions introduced by markers and can provide realistic images for tracking procedures to extract accurate region features. Our simulator also eliminates the need for manually drawing ground truth tumor contours, which can contain large inter- and intra-physician discrepancies.

Our simulator can be extended to simulate real-time patient-specific 4DCT scans for particular synchronized pleural pressure and chest and abdomen height using only the single CT scan as input. In this case, the FE analysis of the lung deformation converges very quickly because there is only a small difference of the lung shape between two time steps. The pleural pressure can be estimated from the lung volume readings through the pressure-volume curve, and yields the precise negative pressure for defining the deformation force.

The synchronized chest and abdomen height yield the patient body outline during respiration, and define the boundary constraints for both lung deformation and 4DCT scan simulation.

The invention provides biomechanical motion model based thoracic 4DCT simulation method for patient lung deformation induced by respiration using only one CT scan as input. The method models lung stress-strain behavior using a hyperelastic Ogden model, and treat the rest of the CT volume as discretized mass points connected by springs and dampers.

This heterogeneous design leverages the advantages of both continuum mechanics and mass-spring-damper system in the way that the lung deformation is determined with high accuracy, while the deformation of the rest of the CT volume is achieved under practical computational constraints. Extensive analysis and comparisons with the manually labeled dataset demonstrate that our lung deformation results are very accurate.

Although the invention has been described by way of examples of preferred embodiments, it is to be understood that various other adaptations and modifications may be made within the spirit and scope of the invention. Therefore, it is the object of the appended claims to cover all such variations and modifications as come within the true spirit and scope of the invention.

We claim:

1. A method for simulating four-dimensional (4D) computed tomography (CT), comprising the steps of:
   generating a first set of volumes from a single thoracic CT scan;
   deforming the first set of volumes according to a biomechanical motion model to obtain a set of deformed volumes;
   constructing a second set of volumes using the set of deformed volumes; and
   deforming the second set of volumes according to a mass-spring model using the CT scan to produce the 4DCT, wherein the steps are performed in a processor.

2. The method of claim 1, wherein the first set of volumes represent a lung, a heart, a diaphragm, a rib cage, and other segmented organs and tissues in the CT scan.

3. The method of claim 1, wherein the first set of volumes is represented by a surface mesh of vertices.

4. The method of claim 2, further comprising:
   generating a lung surface mesh of vertices as the first set of volumes;
   applying tetrahedralization to the lung surface mesh;
   generating boundary constraints and load definitions on the lung surface mesh; and,
   applying finite element (FE) analysis to the lung volume mesh to obtain a lung deformation according to the biomechanical motion model of the lung.

5. The method of claim 4, wherein the biomechanical motion model of the lung is an Ogden model, a Mooney-Rivlin model, a linear elastic model, a linear visco-elastic model, or combinations thereof.

6. The method of claim 4, wherein the boundary constraints consider a lateral displacement of the vertices on upper lobes of the lung is fixed, the lateral displacement of the vertices on and near a convex, hull of the lung surface mesh and around lateral sides of middle and lower lobes of the lung is fixed, and anterioposterior, and superoinferior displacements of the vertices in a vicinity of a thoracic vertebrae are fixed.

7. The method of claim 4, wherein a pressure force inflates the lung surface mesh and a traction force applies to displace the diaphragm along the lateral direction to simulate contraction of pleural sliding of the diaphragm during an inspiration phase of the lung.

8. The method of claim 7, further comprising:
   defining a weight map;
   masking an inner region of the lung by morphological operations to obtain an inner boundary and an outer boundary of the lung;
   sampling the outer boundary and locating corresponding inner points;
   interpolating remaining points;
   construction a ribbon belt from the points;
   building an adjacency graph from the ribbon belt; and
   determining a shortest path for the adjacency graph to obtain an area representing the diaphragm.

9. The method of claim 4, wherein the boundary conditions simulate pleural sliding in a spine region using a set of Gaussian curves.

10. The method of claim 9, further comprising:
    generating a set of two-dimensional axial slices along a lateral direction from the lung volume mesh;
    fitting the Gaussian curves to an area under the lung corresponding to the spine region at each slice by applying a sequential quadratic programming using an active-set that determines a quasi-Newton approximation to a Hessian matrix of a Lagrangian multiplier at each iteration;
    defining a constrained minimization problem using the Gaussian curves;
    removing outliers different to mean Gaussian curve of the set of Gaussian curves; and
    estimating missing curves by linear interpolation.

11. The method of claim 4, wherein the lung is segmented using the single thoracic CT scan to generate the lung surface mesh.

12. The method of claim 9, wherein the tetrahedralization considers loads on the rib cage and the diaphragm.

13. The method of claim 1, further comprising:
    applying constrained tetrahedralization, using control points, to the set of deformed volumes to obtain the second volume mesh; and
    deforming the second volume mesh using the mass-spring model to produces the 4DCT.

14. The method of claim 13, wherein the second volume covers the set of deformed volumes outside the set of first volume meshes.

15. The method of claim 13, wherein the mass-spring model treats the set of second volumes as a discrete structure of internal springs where parameters of mass, damping forces, and constants, are assigned to vertices in the second set of volumes by converting image values of the CT scan, and the displacement between the first volume mesh and deformed mesh generates tension parameters for the internal springs by Hooke's Law after each lung deformation.

16. The method of claim 1, wherein the simulation is between a maximal exhale phase and the maximal inhale phase during, the lung deformation with or without hysteresis of tissue deformation.

17. The method of claim 1, further comprising:
    embedding a tumor into the set of first volumes by determining barycentric coordinates of vertices of the tumor to nearby lung tetrahedra.

18. A method for simulating computed tomography (CT), comprising the steps of:

generating a surface mesh from a single thoracic CT scan;
applying tetrahedralization to the surface mesh to obtain a first volume mesh;
applying finite element (FE) analysis to the first volume mesh, using boundary constraints and load definitions, to obtain a lung deformation according to an Ogden model;
applying constrained tetrahedralization, using control points, to the lung deformation to obtain a second volume mesh; and
deforming the second volume mesh using mass-spring-damper simulation to produces the CT, wherein the steps are performed in a processor.

* * * * *